(12) United States Patent
Noguchi et al.

(10) Patent No.: US 11,903,762 B2
(45) Date of Patent: Feb. 20, 2024

(54) ULTRASOUND PROBE

(71) Applicant: FUJIFILM Corporation, Tokyo (JP)

(72) Inventors: Shinsuke Noguchi, Kanagawa (JP); Ryosuke Ogura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/218,275

(22) Filed: Mar. 31, 2021

(65) Prior Publication Data

US 2021/0212663 A1 Jul. 15, 2021

Related U.S. Application Data

(63) Continuation of application No. PCT/JP2019/038731, filed on Oct. 1, 2019.

(30) Foreign Application Priority Data

Oct. 11, 2018 (JP) .................. 2018-192568

(51) Int. Cl.
*A61B 8/00* (2006.01)

(52) U.S. Cl.
CPC .......... *A61B 8/4455* (2013.01); *A61B 8/4488* (2013.01); *A61B 8/4281* (2013.01); *A61B 8/4472* (2013.01)

(58) Field of Classification Search
CPC .... A61B 8/4455; A61B 8/4488; A61B 8/4422
See application file for complete search history.

(56) References Cited

U.S. PATENT DOCUMENTS

| 2004/0181154 A1* | 9/2004 | Peterson | ............. A61B 8/4472 600/459 |
|---|---|---|---|
| 2006/0100513 A1 | 5/2006 | Hashimoto | |

(Continued)

FOREIGN PATENT DOCUMENTS

| CN | 1874615 A | 12/2006 |
|---|---|---|
| CN | 102068278 A | 5/2011 |

(Continued)

OTHER PUBLICATIONS

The extended European search report issued by the European Patent Office dated Nov. 18, 2021, which corresponds to European Patent Application No. 19871992.4-1126 and is related to U.S. Appl. No. 17/218,275.

(Continued)

*Primary Examiner* — Colin T. Sakamoto
*Assistant Examiner* — Tommy T Ly
(74) *Attorney, Agent, or Firm* — Studebaker & Brackett PC

(57) ABSTRACT

An ultrasound probe 11 includes a transducer array in which a plurality of transducers are arranged, and a housing 12 in which the transducer array is accommodated. The housing 12 has a grip portion 13 that extends in a determined direction, and a transducer array accommodation portion 14 that is connected to one end portion of the grip portion 13 in an extension direction and accommodates the transducer array. A probe support surface 13B that extends along the extension direction is defined in a surface on the other end portion side of the grip portion 13 in the extension direction. In a case where the ultrasound probe is placed on a flat placing surface with the probe support surface 13B being brought into contact with the placing surface, the ultrasound probe is in such a posture that a surface of the housing 12 in a portion positioned on the transducer array accommodation portion 14 side with respect to the probe support surface 13B is separated from the placing surface.

6 Claims, 5 Drawing Sheets

(56) References Cited

U.S. PATENT DOCUMENTS

| | | | |
|---|---|---|---|
| 2006/0229530 A1* | 10/2006 | Hosoda | A61B 5/150022 600/573 |
| 2008/0194960 A1* | 8/2008 | Randall | A61B 8/00 600/459 |
| 2008/0228081 A1* | 9/2008 | Becker | A61B 8/4461 600/459 |
| 2009/0137905 A1 | 5/2009 | Watson et al. | |
| 2012/0078111 A1* | 3/2012 | Tanabe | A61B 8/56 600/459 |
| 2015/0276685 A1 | 10/2015 | Yasuhara et al. | |
| 2017/0252465 A1 | 9/2017 | Nagai et al. | |
| 2018/0110497 A1* | 4/2018 | Beacham | A61B 8/4455 |
| 2018/0125449 A1 | 5/2018 | Mauldin, Jr. et al. | |

FOREIGN PATENT DOCUMENTS

| | | |
|---|---|---|
| CN | 104768472 A | 7/2015 |
| CN | 107005770 A | 8/2017 |
| EP | 1728563 B1 | 8/2021 |
| JP | S55-148545 A | 11/1980 |
| JP | 2004290414 A | 10/2004 |
| JP | 2006-026236 A | 2/2006 |
| JP | 2007-117127 A | 5/2007 |
| JP | 2007-175081 A | 7/2007 |

OTHER PUBLICATIONS

Optional Probes, Aloka Co., Ltd., Feb. 2002, pp. 1-10, Catalog.

International Search Report issued in PCT/JP2019/038731; dated Nov. 26, 2019.

International Preliminary Report On Patentability and Written Opinion issued in PCT/JP2019/038731; dated Apr. 8, 2021.

An Office Action; "Notice of Reasons for Refusal," mailed by the Japanese Patent Office dated Jan. 31, 2023, which corresponds to Japanese Patent Application No. 2022-031559 and is related to U.S. Appl. No. 17/218,275; with English language translation.

An Office Action mailed by The State Intellectual Property Office of People's Republic of China dated Jun. 27, 2023, which corresponds to Chinese Patent Application No. 201980066735.5 and is related to U.S. Appl. No. 17/218,275; with English translation.

Communication pursuant to Article 94(3) EPC issued by the European Patent Office dated May 25, 2023, which corresponds to European Patent Application No. 19871992.4-1126 and is related to U.S. Appl. No. 17/218,275.

An Office Action mailed by China National Intellectual Property Administration dated Oct. 21, 2023, which corresponds to Chinese Patent Application No. 201980066735.5. and is related to U.S. Appl. No. 17/218,275; with English language translation.

* cited by examiner

ULTRASOUND PROBE

CROSS-REFERENCE TO RELATED APPLICATIONS

This application is a Continuation of PCT International Application No. PCT/JP2019/038731 filed on Oct. 1, 2019, which claims priority under 35 U.S.C. § 119(a) to Japanese Patent Application No. 2018-192568 filed on Oct. 11, 2018. The above application is hereby expressly incorporated by reference, in its entirety, into the present application.

BACKGROUND OF THE INVENTION

1. Field of the Invention

The present invention relates to an ultrasound probe, and in particular, to an ultrasound probe in which ultrasound gel for adjusting acoustic impedance is applied to a distal end portion coming into contact with a subject during an examination.

2. Description of the Related Art

Hitherto, in a medical field, an ultrasound diagnostic apparatus using an ultrasound image has come into practical use. In general, this kind of ultrasound diagnostic apparatus has an ultrasound probe that incorporates a transducer array, and an apparatus body connected to the ultrasound probe. The ultrasound probe transmits ultrasonic waves toward a subject and receives ultrasound echoes from the subject, and the apparatus body electrically processes reception signals to generate an ultrasound image.

In transmitting the ultrasonic wave from the ultrasound probe toward the subject, in a case where a gap occurs between the subject and a distal end portion of the ultrasound probe coming into contact with the subject and a layer of air is present, a difference in acoustic impedance between the distal end portion of the ultrasound probe and the subject increases due to the layer of air, and the ultrasonic wave is attenuated and reflected. Accordingly, for example, as disclosed in JP2007-175081A, ultrasound gel that fills the gap between the subject and the distal end portion of the ultrasound probe coming into contact with the subject is applied to the distal end portion of the ultrasound probe, thereby restraining attenuation and the reflection of the ultrasonic wave between the distal end portion of the ultrasound probe and the subject.

SUMMARY OF THE INVENTION

Incidentally, in the middle of executing an examination on the subject using the ultrasound probe, a user may place the ultrasound probe on a desk in the vicinity of the subject, a bed, or the like depending on the circumstances of the examination. In a case where the ultrasound probe is placed on the desk or the bed in a state in which the ultrasound gel is applied to the distal end portion of the ultrasound probe, the ultrasound gel is stuck to the desk, the bed, or the like to soil the desk, the bed, or the like or the ultrasound gel itself is soiled due to being stuck to the desk, the bed, or the like.

The invention has been accomplished to solve such a problem in the related art, and an object of the invention is to provide an ultrasound probe that restrains ultrasound gel from being stuck to a placing surface on which the ultrasound probe is placed.

To achieve the above-described object, an aspect of the invention provides an ultrasound probe comprising a transducer array in which a plurality of transducers are arranged, and a housing in which the transducer array is accommodated. The housing has a grip portion that extends in a determined direction, and a transducer array accommodation portion that is connected to one end portion of the grip portion in the extension direction and accommodates the transducer array. A probe support surface that extends along the extension direction is defined in a surface on the other end portion side of the grip portion in the extension direction. In a case where the ultrasound probe is placed on a flat placing surface with the probe support surface being brought into contact with the placing surface, the ultrasound probe is in such a posture that a surface of the housing in a portion positioned on the transducer array accommodation portion side with respect to the probe support surface is separated from the placing surface.

It is preferable that a center of gravity of the ultrasound probe is positioned on the other end portion side of the grip portion in the extension direction of the grip portion.

In this case, it is preferable that the center of gravity is positioned between the probe support surface and a probe reference surface that passes through a center of the arrangement of the plurality of transducers in the transducer array and extends in an arrangement direction of the plurality of transducers and the extension direction of the grip portion.

In this case, it is preferable that the ultrasound probe further comprises a battery that is incorporated in the other end portion of the grip portion.

It is preferable that the other end portion of the grip portion has an appearance asymmetrical about the probe reference surface.

In this case, it is preferable that the housing has a probe operating surface that is defined in a surface of the other end portion of the grip portion and is directed in a direction opposite to the probe support surface, the probe reference surface is positioned between the probe support surface and the probe operating surface, and a distance between the probe reference surface and the probe support surface is greater than a distance between the probe reference surface and the probe operating surface.

The ultrasound probe may comprise an operation switch and an indicator disposed in the probe operating surface.

The housing may have a protrusion that is formed at a position on a surface on the same side as the probe support surface about the probe reference surface and close to the transducer array accommodation portion with respect to the probe support surface, and the ultrasound probe is in such a posture that, in a case where the ultrasound probe is placed on the placing surface with the probe support surface being brought into contact with the placing surface, a surface of the protrusion is separated from the placing surface, and in a case where the ultrasound probe is placed on the placing surface with the protrusion being brought into contact with the placing surface, a surface of the transducer array accommodation portion is separated from the placing surface.

According to the invention, the ultrasound probe comprises the transducer array in which a plurality of transducers are arranged, and the housing in which the transducer array is accommodated. The housing has the grip portion that extends in the determined direction, and the transducer array accommodation portion that is connected to the one end portion of the grip portion in the extension direction and accommodates the transducer array. The probe support surface that extends along the extension direction is defined in the surface on the other end portion side of the grip portion in the extension direction. In a case where the ultrasound probe is placed on the flat placing surface with the probe support surface being brought into contact with the placing surface, the ultrasound probe is in such a posture that the surface of the housing in the portion positioned on the transducer array accommodation portion side with respect to the probe support surface is separated from the placing surface. Thus, it is possible to restrain ultrasound gel from being stuck to the placing surface on which the ultrasound probe is placed.

DESCRIPTION OF THE PREFERRED EMBODIMENTS

Hereinafter, embodiments of the invention will be described referring to the accompanying drawings.

Embodiment 1

Figure 1:
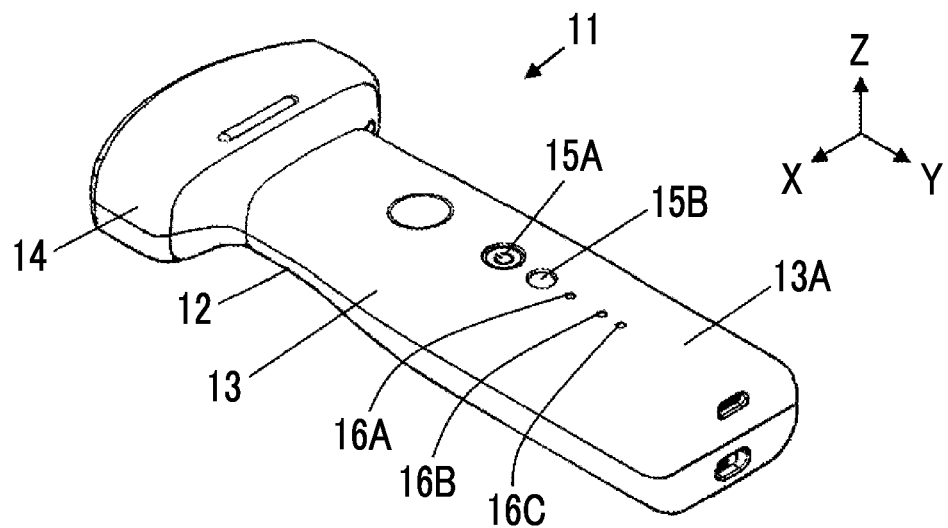
FIG. 1 is a perspective view of an ultrasound probe according to Embodiment 1 of the invention viewed from above.

FIG. 1 shows an ultrasound probe 11 according to an embodiment of the invention. As shown in FIG. 1, the ultrasound probe 11 comprises a housing 12, and the housing 12 has a grip portion 13 that extends in a determined direction and has a wide and flat cross-sectional shape, and a transducer array accommodation portion 14 that is connected to one end portion of the grip portion 13. The transducer array accommodation portion 14 is formed to be wider and thicker than the grip portion 13. A probe operating surface 13A is defined in a surface of the other end portion of the grip portion 13, and operation switches 15A and 15B of the ultrasound probe 11 and indicators 16A, 16B, and 16C are disposed in the probe operating surface 13A.

Hereinafter, for description, a direction from the transducer array accommodation portion 14 toward the grip portion 13 along a direction in which the grip portion 13 extends is referred to as a +Y direction, a width direction of the grip portion 13 perpendicular to the Y direction is referred to as an X direction, and a thickness direction of the ultrasound probe 11 perpendicular to the Y direction and the X direction is referred to as a Z direction. The probe operating surface 13A of the grip portion 13 is defined in a surface on a +Z direction side of the grip portion 13.

Figure 2:
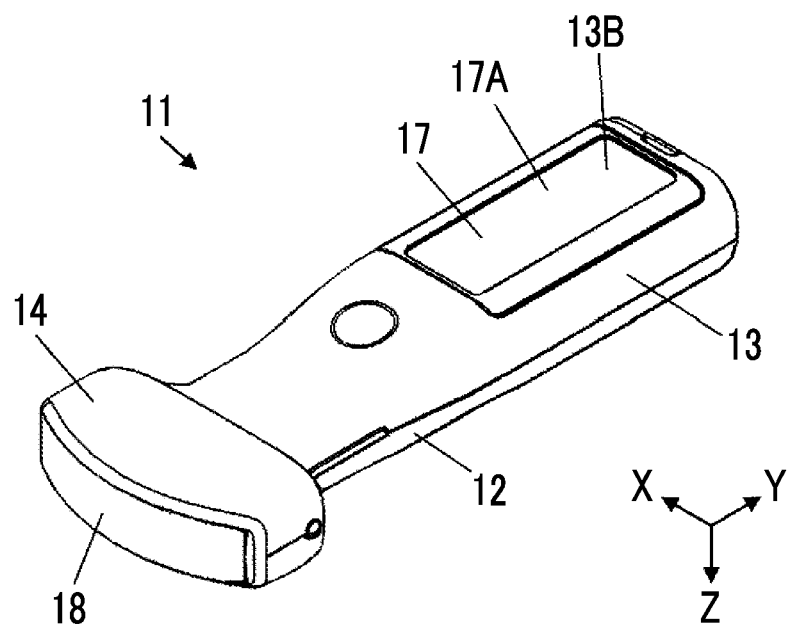
FIG. 2 is a perspective view of the ultrasound probe according to Embodiment 1 of the invention viewed from below.

As shown in FIG. 2, an attachable and detachable battery cover 17 is disposed on a −Z direction side of the other end portion of the grip portion 13. A flat surface 17A along an XY plane is formed in a surface of the battery cover 17, and a flat probe support surface 13B along the XY plane is defined on the −Z-direction side of the other portion of the grip portion 13 by the flat surface 17A of the battery cover 17.

An acoustic lens 18 is disposed in an end portion of the transducer array accommodation portion 14 in a −Y direction.

Figure 3:
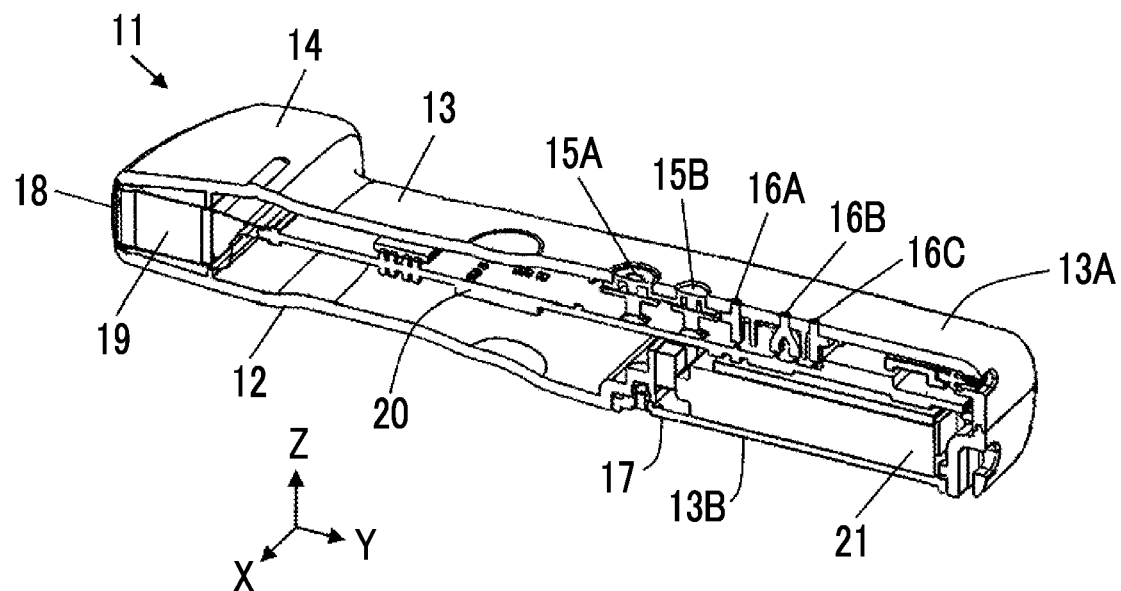
FIG. 3 is a cross-sectional view of the ultrasound probe according to Embodiment 1 of the invention.

FIG. 3 is a sectional view of the ultrasound probe 11 along an YZ plane passing through the operation switches 15A and 15B and the indicators 16A to 16C. As shown in FIG. 3, the transducer array 19 is accommodated in the transducer array accommodation portion 14, and a circuit substrate 20 is disposed in the housing 12 from the transducer array accommodation portion 14 to an end portion of the grip portion 13 in the +Y direction. Here, the transducer array 19 has a plurality of transducers arranged along the XY plane, and is connected to the circuit substrate 20 through a plurality of wirings.

A battery 21 is incorporated in the end portion of the grip portion 13 in the +Y direction on the −Z direction side with respect to the circuit substrate 20, and the battery 21 is connected to the circuit substrate 20.

The battery 21 is covered with the attachable and detachable battery cover 17, and can be replaced by detaching the battery cover 17.

The operation switches 15A and 15B and the indicators 16A to 16C are connected to the circuit substrate 20. The operation switches 15A and 15B are operated by the user, for example, for supply of power of the ultrasound probe 11, cutoff of power of the ultrasound probe 11, and an instruction of the operation of the ultrasound probe 11. The indicators 16A to 16C are constituted of, for example, a light emitting diode (LED), and emit light in response to a signal from the circuit substrate 20 to perform various kinds of notification, such as a supply state of power, a remaining capacity of the battery 21, and an operation state of the ultrasound probe 11.

Here, the ultrasound probe 11 is used to transmit and receive ultrasonic waves to and from a subject with the transducer array 19 to capture an ultrasound image representing a tomographic plane of the subject, and is connected to a diagnostic apparatus body that generates and displays the ultrasound image based on signals acquired by the ultrasound probe 11 as described below.

Figure 4:
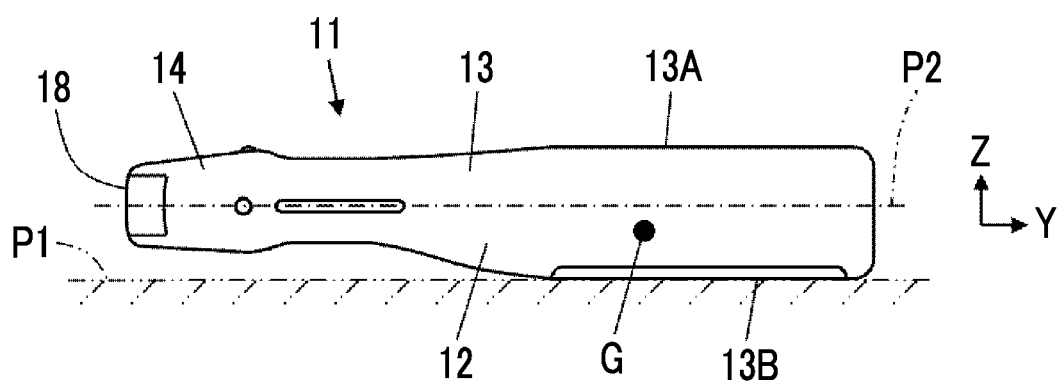
FIG. 4 is a side view of the ultrasound probe according to Embodiment 1 of the invention.

As shown in FIG. 4, in a case where the ultrasound probe 11 is placed on a flat placing surface P1 with the probe support surface 13B being brought into contact with the placing surface P1, the ultrasound probe 11 is configured to be in such a posture that a surface of the housing 12 in a portion positioned on the transducer array accommodation portion 14 side with respect to the probe support surface 13B is separated from the placing surface P1.

Here, in a case where the XY plane that passes through the center of the arrangement of a plurality of transducers in the transducer array 19 and extends in the arrangement direction of a plurality of transducers and an extension direction of the grip portion 13 is referred to as a probe reference surface P2, the end portion of the grip portion 13 in the +Y direction has an appearance asymmetrical about the probe reference surface P2. More specifically, a thickness in the Z direction of the grip portion 13 on the −Z direction side from the probe reference surface P2 is thicker than a thickness in the Z direction of the grip portion 13 on the +Z direction side from the probe reference surface P2. For this reason, a distance between the probe reference surface P2 and the probe support surface 13B is greater than a distance between the probe reference surface P2 and the probe operating surface 13A, and in a case where the ultrasound probe 11 is placed on the flat placing surface P1 with the probe support surface 13B being brought into contact with the placing surface P1, the surface of the housing 12 in the portion positioned on the transducer array accommodation portion 14 side with respect to the probe support surface 13B is formed to be easily separated from the placing surface P1 in the +Z direction.

As shown in FIG. 3, the ultrasound probe 11 incorporates the battery 21 that is a heavy load directly above the battery cover 17 forming the probe support surface 13B. For this reason, as shown in FIG. 4, a center of gravity G of the ultrasound probe 11 is positioned on the end portion side of the grip portion 13 in the +Y direction and between the probe reference surface P2 and the probe support surface 13B. With this, in a case where the ultrasound probe 11 is placed on the placing surface P1 such that the probe support surface 13B is brought into contact with the placing surface P1 with the extension direction of the grip portion 13 set horizontal, the ultrasound probe 11 can be stabilized in such a posture that the surface of the housing 12 in the portion positioned on the transducer array accommodation portion 14 side with respect to the probe support surface 13B is separated from the placing surface P1.

Here, in performing an examination of the subject using the ultrasound probe 11, in a case where a gap occurs between the acoustic lens 18 and the subject and a layer of air is present, a difference in acoustic impedance between the acoustic lens 18 and the subject increases due to the layer of air, and the ultrasonic wave is attenuated and reflected. Therefore, so-called ultrasound gel is applied to the end portion of the acoustic lens 18 and the end portion of the transducer array accommodation portion 14 in the −Y direction, whereby it is possible to restrain the occurrence of a significant difference in acoustic impedance between the acoustic lens 18 and the subject.

With the ultrasound probe 11 according to Embodiment 1 of the invention, in a case where the ultrasound probe 11 is placed on the placing surface P1, the ultrasound probe 11 is in such a posture that the surface of the housing 12 in the portion positioned on the transducer array accommodation portion 14 side with respect to the probe support surface 13B is separated from the placing surface P1. Thus, even though the ultrasound probe 11 is placed on the placing surface P1 in a state in which so-called ultrasound gel is applied to the acoustic lens 18 and the end portion of the transducer array accommodation portion 14 in the −Y direction, it is possible to restrain the ultrasound gel from being stuck to the placing surface P1 and soiling the placing surface P1. It is also possible to restrain the ultrasound gel itself from being soiled due to the ultrasound gel applied to the ultrasound probe 11 being stuck to the placing surface P1.

The housing 12 of the ultrasound probe 11 has the probe operating surface 13A that is directed in a direction opposite to the probe support surface 13B, and the operation switches 15A and 15B and the indicators 16A to 16C are disposed in the probe operating surface 13A. Thus, in a case where the user places the ultrasound probe 11 on the placing surface P1, it is possible to attract user's attention such that the probe operating surface 13A where the operation switches 15A and 15B and the indicators 16A to 16C are disposed is directed upward, that is, the probe support surface 13B is directed downward and is brought into with the placing surface P1.

Figure 5:
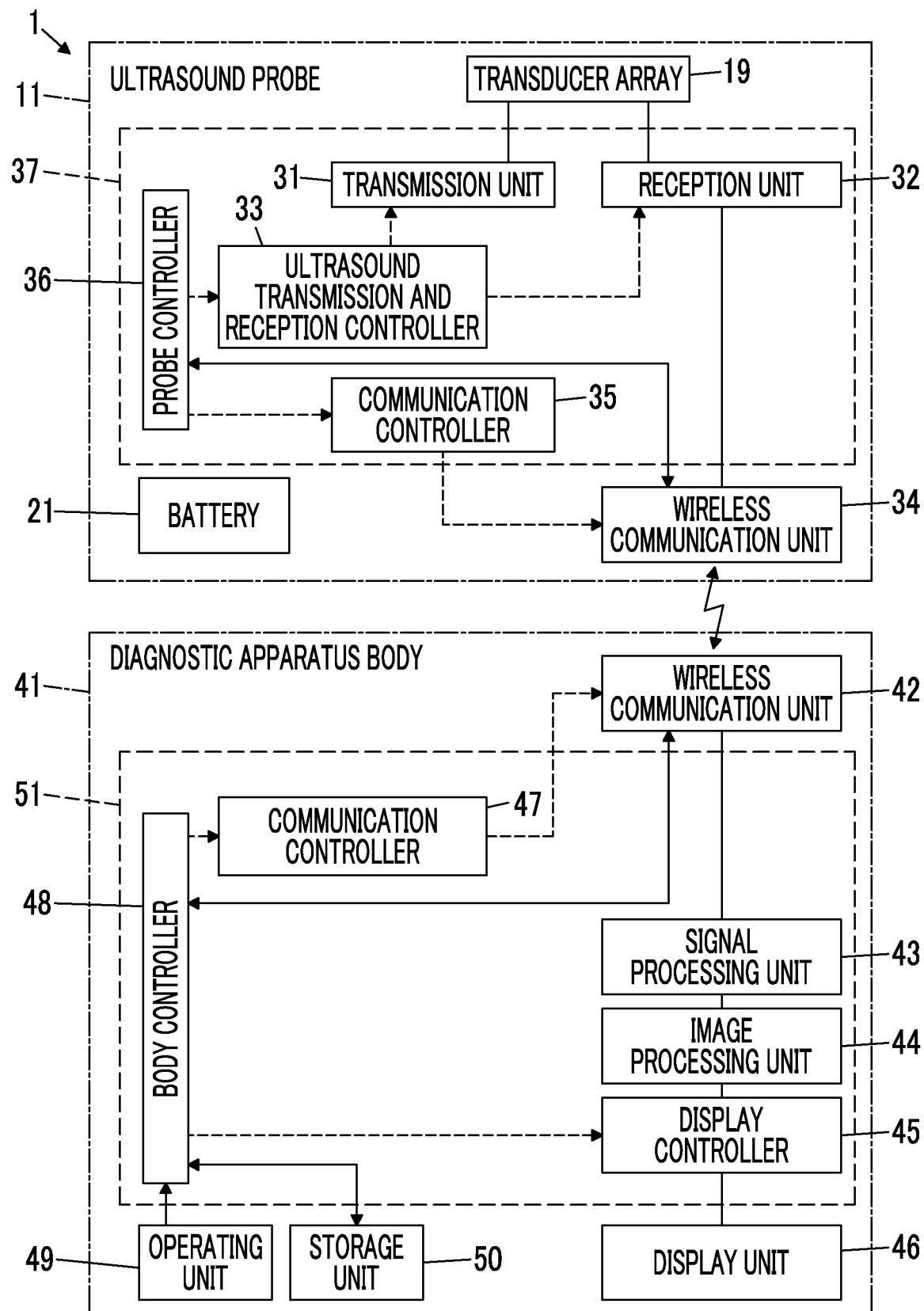
FIG. 5 is a block diagram showing the configuration of an ultrasound diagnostic apparatus comprising the ultrasound probe according to Embodiment 1 of the invention.

Next, an ultrasound diagnostic apparatus 1 comprising the ultrasound probe 11 according to Embodiment 1 of the invention will be described. FIG. 5 shows the configuration of the ultrasound diagnostic apparatus 1. As shown in FIG. 5, the ultrasound diagnostic apparatus 1 comprises the ultrasound probe 11 according to Embodiment 1 of the invention and a diagnostic apparatus body 41, and the ultrasound probe 11 and the diagnostic apparatus body 41 are connected through wireless communication.

The ultrasound probe 11 comprises the transducer array 19, and a transmission unit 31 and a reception unit 32 are connected to the transducer array 19. An ultrasound transmission and reception controller 33 is connected to the transmission unit 31 and the reception unit 32. A wireless communication unit 34 is connected to the reception unit 32, and a communication controller 35 is connected to the wireless communication unit 34. A probe controller 36 is connected to the ultrasound transmission and reception controller 33, the wireless communication unit 34, and the communication controller 35. Here, the wireless communication unit 34 and the probe controller 36 are connected in such a manner that information can be transferred in two directions. The ultrasound probe 11 incorporates the battery 21.

The transmission unit 31, the reception unit 32, the ultrasound transmission and reception controller 33, the communication controller 35, and the probe controller 36 constitute an ultrasound probe-side processor 37.

The diagnostic apparatus body 41 comprises a wireless communication unit 42, and a signal processing unit 43, an image processing unit 44, a display controller 45, and a display unit 46 are sequentially connected to the wireless communication unit 42. A communication controller 47 is connected to the wireless communication unit 42, and a body controller 48 is connected to the wireless communication unit 42, the communication controller 47, and the display controller 45. An operating unit 49 and a storage unit 50 are connected to the body controller 48. Here, the wireless communication unit 42 and the body controller 48, and the body controller 48 and the storage unit 50 are connected in such a manner that information can be transferred in two directions.

The signal processing unit 43, the image processing unit 44, the display controller 45, the communication controller 47, and the body controller 48 constitute a diagnostic apparatus body-side processor 51.

The wireless communication unit 34 of the ultrasound probe 11 and the wireless communication unit 42 of the diagnostic apparatus body 41 are connected in such a manner that information can be transferred in two directions. With this, the ultrasound probe 11 and the diagnostic apparatus body 41 are connected through wireless communication.

The transducer array 19 of the ultrasound probe 11 shown in FIG. 5 has a plurality of transducers arranged in a one-dimensional or two-dimensional manner. The transducers transmit ultrasonic waves in compliance with drive signals supplied from the transmission unit 31, receive ultrasound echoes from the subject, and output reception signals. Each transducer is constituted by forming electrodes at both ends of a piezoelectric body consisting of, for example, piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The ultrasound transmission and reception controller 33 of the ultrasound probe-side processor 37 performs control such that the transmission unit 31 and the reception unit 32 perform transmission of an ultrasonic beam and reception of ultrasound echoes based on an instruction from the probe controller 36, respectively.

The transmission unit 31 of the ultrasound probe-side processor 37 includes, for example, a plurality of pulse generators, and adjusts a delay amount of each drive signal based on a transmission delay pattern selected in response to a control signal from the ultrasound transmission and reception controller 33 such that ultrasonic waves transmitted from a plurality of transducers of the transducer array 19 form an ultrasonic beam, and supplies the drive signals to a plurality of transducers. In this way, in a case where a pulsed or continuous-wave voltage is applied to the electrodes of each of a plurality of transducers of the transducer array 19, the piezoelectric body expands and contracts to generate a pulsed or continuous-wave ultrasonic wave from each of the transducers. An ultrasonic beam is formed from a combined wave of the ultrasonic waves.

The transmitted ultrasonic beam is reflected by, for example, a target, such as a part of the subject, and propagates toward the transducer array 19 of the ultrasound probe 11. The ultrasound echo propagating toward the transducer array 19 is received by each transducer constituting the transducer array 19. In this case, each transducer constituting the transducer array 19 expands and contracts with reception of the propagating ultrasound echo to generate an electrical signal, and outputs the electrical signal to the reception unit 32.

Figure 6:
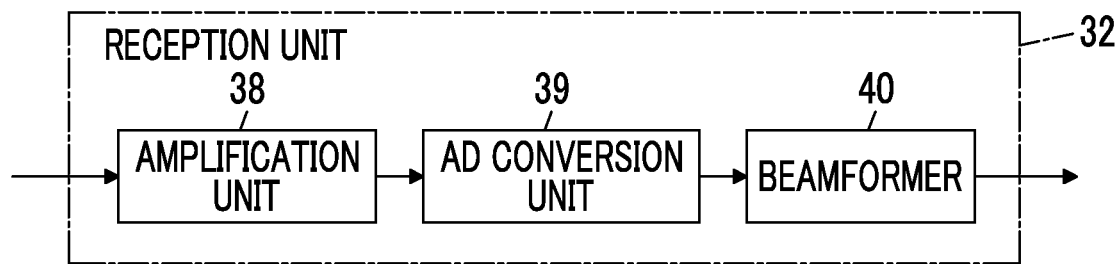
FIG. 6 is a block diagram showing the internal configuration of a reception unit in Embodiment 1 of the invention.

The reception unit 32 of the ultrasound probe-side processor 37 executes processing of the reception signals output from the transducer array 19 in compliance with a control signal from the ultrasound transmission and reception controller 33. As shown in FIG. 6, the reception unit 32 has a configuration in which an amplification unit 38, an analog-digital (AD) conversion unit 39, and a beamformer 40 are connected in series. The amplification unit 38 amplifies the reception signal input from each of the transducers constituting the transducer array 19 and transmits the amplified reception signal to the AD conversion unit 39. The AD conversion unit 39 converts the reception signal transmitted from the amplification unit 38 into digitized data and sends the digitized data to the beamformer 40. The beamformer 40 executes reception focus processing of giving a delay to each piece of data compliant with a set sound speed based on a reception delay pattern selected in response to a control signal from the ultrasound transmission and reception controller 33 and performing addition (phasing addition). With the reception focus processing, a sound ray signal in which a focus of the ultrasound echo is narrowed on a given scanning line is generated. The sound ray signal generated in this manner is sent to the wireless communication unit 34 of the ultrasound probe 11.

The wireless communication unit 34 of the ultrasound probe 11 includes an antenna that performs transmission and reception of radio waves, and performs wireless communication with the wireless communication unit 42 of the diagnostic apparatus body 41. In this case, the wireless communication unit 34 modulates a carrier based on the sound ray signal sent from the reception unit 32 to generate a transmission signal and transmits the generated transmission signal to the wireless communication unit 42 of the diagnostic apparatus body 41 in a wireless manner. As a modulation system of the carrier, for example, amplitude shift keying (ASK), phase shift keying (PSK), quadrature phase shift keying (QPSK), 16 quadrature amplitude modulation (16QAM), or the like is used.

The communication controller 35 of the ultrasound probe-side processor 37 performs control such that the wireless communication unit 34 of the ultrasound probe 11 transmits the sound ray signal with transmission field intensity set by the probe controller 36.

The probe controller 36 of the ultrasound probe-side processor 37 performs control of each unit of the ultrasound probe 11 based on a program or the like stored in advance.

The battery 21 of the ultrasound probe 11 is incorporated in the ultrasound probe 11, and supplies electric power to each circuit of the ultrasound probe 11.

The wireless communication unit 42 of the diagnostic apparatus body 41 includes an antenna that performs transmission and reception of radio waves, and performs wireless communication with the wireless communication unit 34 of the ultrasound probe 11. In this case, the wireless communication unit 42 of the diagnostic apparatus body 41 outputs a sound ray signal, for example, by receiving the transmission signal transmitted from the wireless communication unit 34 of the ultrasound probe 11 in a wireless manner through the antenna and demodulating the received transmission signal. The wireless communication unit 42 of the diagnostic apparatus body 41 sends the sound ray signal output in this manner to the signal processing unit 43.

The signal processing unit 43 of the diagnostic apparatus body-side processor 51 performs correction of attenuation of the sound ray signal sent from the wireless communication unit 42 due to a propagation distance depending on a depth of a reflection position of the ultrasonic wave, and then, executes envelope detection to generate a signal as tomographic image information regarding a tissue in the subject.

The image processing unit 44 of the diagnostic apparatus body-side processor 51 generates an ultrasound image signal by raster-converting the signal generated by the signal processing unit 43 into an image signal in compliance with a normal television signal scanning system and executing various kinds of necessary image processing, such as brightness correction, tone correction, sharpness correction, and color correction, on the image signal generated in this manner. The image processing unit 44 sends the ultrasound image signal generated in this manner to the display controller 45.

The display controller 45 of the diagnostic apparatus body-side processor 51 executes predetermined processing on the ultrasound image signal generated by the image processing unit 44 and displays an ultrasound image on the display unit 46 under the control of the body controller 48.

The display unit 46 of the diagnostic apparatus body 41 displays an image under the control of the display controller 45, and includes, for example, a display device, such as a liquid crystal display (LCD), an organic electroluminescence display (organic EL display).

The communication controller 47 of the diagnostic apparatus body-side processor 51 performs control such that the wireless communication unit 42 of the diagnostic apparatus body 41 receives the transmission signal from the wireless communication unit 34 of the ultrasound probe 11.

The body controller 48 of the diagnostic apparatus body-side processor 51 performs control of each unit of the diagnostic apparatus body 41 based on a program stored in advance in the storage unit 50 or the like and a user's operation through the operating unit 49.

The operating unit 49 of the diagnostic apparatus body 41 is provided for the user to perform an input operation, and can comprise a keyboard, a mouse, a trackball, a touch pad, a touch panel, and the like.

The storage unit 50 of the diagnostic apparatus body 41 stores an operation program and the like of the diagnostic apparatus body 41, and as the storage unit 50, a recording medium, such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), a server, or the like can be used.

Here, in the ultrasound probe 11, each of the ultrasound probe-side processor 37 having the transmission unit 31, the reception unit 32, the ultrasound transmission and reception controller 33, the communication controller 35, and the probe controller 36 and the diagnostic apparatus body-side processor 51 having the signal processing unit 43, the image processing unit 44, the display controller 45, the communication controller 47, and the body controller 48 is constituted of a central processing unit (CPU) and a control program causing the CPU to execute various kinds of processing. However, the ultrasound probe-side processor 37 and the diagnostic apparatus body-side processor 51 may be constituted using a field programmable gate array (FPGA), a digital signal processor (DSP), an application specific integrated circuit (ASIC), or other integrated circuits (ICs) or may be constituted by combining the IC circuits.

The transmission unit 31, the reception unit 32, the ultrasound transmission and reception controller 33, the communication controller 35, and the probe controller 36 of the ultrasound probe-side processor 37 may be constituted to be partially or wholly integrated into one CPU or the like. The signal processing unit 43, the image processing unit 44, the display controller 45, the communication controller 47, and the body controller 48 of the diagnostic apparatus body-side processor 51 may be constituted to be partially or wholly integrated into one CPU or the like.

Although the grip portion 13 in Embodiment 1 has a wide and flat cross-sectional shape, the shape of the grip portion 13 is not particularly limited as long as the probe support surface 13B is formed, and in a case where the ultrasound probe 11 is placed on the placing surface P1, the ultrasound probe 11 is in such a posture that the surface of the housing 12 in the portion positioned on the transducer array accommodation portion 14 side with respect to the probe support surface 13B is separated from the placing surface P1.

Although the housing 12 of the ultrasound probe 11 of Embodiment 1 has a shape asymmetrical about the probe reference surface P2, the housing 12 can also have a shape symmetrical about the probe reference surface P2 as long as the distance between the probe reference surface P2 and the probe support surface 13B is sufficiently separated, and in a case where the ultrasound probe 11 is placed on the placing surface P1, the ultrasound probe 11 is in such a posture that the surface of the housing 12 in the portion positioned on the transducer array accommodation portion 14 side with respect to the probe support surface 13B is separated from the placing surface P1.

Here, in a case where the ultrasound probe 11 is placed on the placing surface P1, to set the housing 12 in a shape symmetrical about the probe reference surface P2 while setting the ultrasound probe 11 in such a posture that the surface of the housing 12 in the portion positioned on the transducer array accommodation portion 14 side with respect to the probe support surface 13B is separated from the placing surface P1, there is a need to design such that a thickness of a portion of the grip portion 13 on the +Z direction side with respect to the probe reference surface P2 is equal to a thickness of a portion of the grip portion 13 on the −Z direction side with respect to the probe reference surface P2. In this case, since the grip portion 13 is thickened, the user hardly grips the grip portion 13, and there is a concern that a user's operation of the ultrasound probe 11 is hindered. For this reason, while the housing 12 of the ultrasound probe 11 can have a shape symmetrical about the probe reference surface P2, it is preferable that the housing 12 has a shape asymmetrical about the probe reference surface P2.

While the ultrasound diagnostic apparatus 1 has the diagnostic apparatus body 41 that is connected to the ultrasound probe 11 in a wireless manner, the ultrasound diagnostic apparatus 1 may have a diagnostic apparatus body that is connected to the ultrasound probe 11 in a wired manner, instead of the diagnostic apparatus body 41.

In a case where an ultrasound probe is used in combination with a portable diagnostic apparatus body with no so-called probe holder for holding the ultrasound probe, the ultrasound probe is often placed, for example, on a desk in the vicinity of a subject or a bed, and the ultrasound probe 11 of Embodiment 1 of the invention is particularly useful.

Embodiment 2

Figure 7:
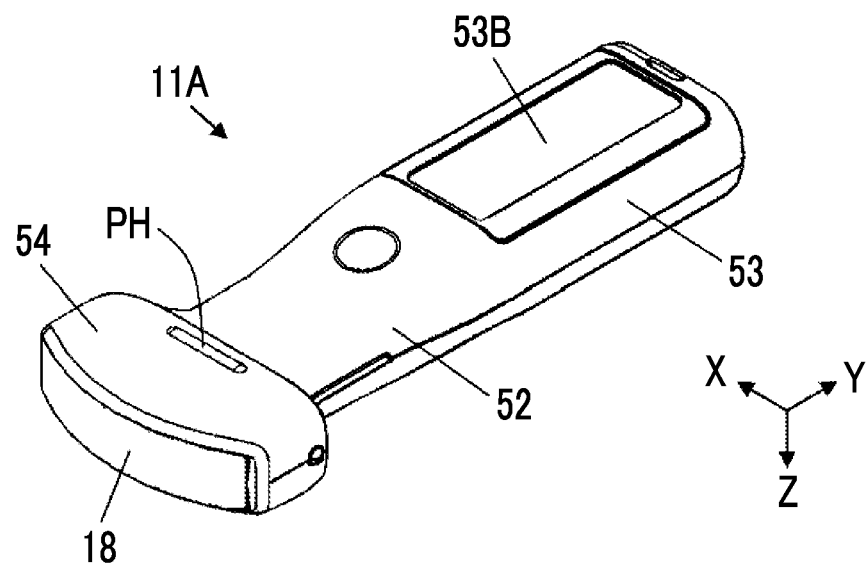
FIG. 7 is a perspective view of an ultrasound probe according to Embodiment 2 of the invention viewed from below.

FIG. 7 shows an ultrasound probe 11A according to Embodiment 2 of the invention. The ultrasound probe 11A comprises a housing 52 instead of the housing 12 in the ultrasound probe 11 of Embodiment 1 shown in FIGS. 1 to 4. As shown in FIG. 7, the housing 52 has a grip portion 53 that extends in the Y direction, and a transducer array accommodation portion 54 that is connected to an end portion of the grip portion 53 in the −Y direction. A flat probe support surface 53B along the XY plane is formed in a surface on the −Z direction side of the grip portion 53. In the housing 52, a protrusion PH that protrudes in the −Z direction is formed on a surface on the same −Z direction side as the probe support surface 53B and on the transducer array accommodation portion 54 side with respect to the probe support surface 53B.

Figure 8:
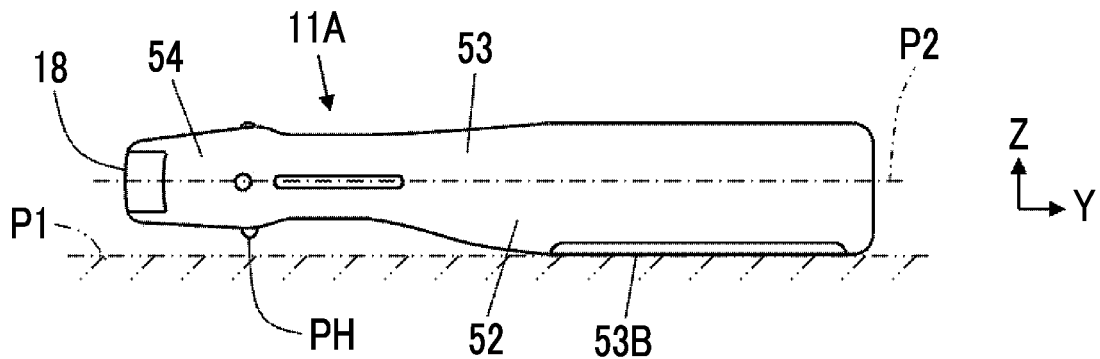
FIG. 8 is a side view of the ultrasound probe according to Embodiment 2 of the invention.
Figure 9:
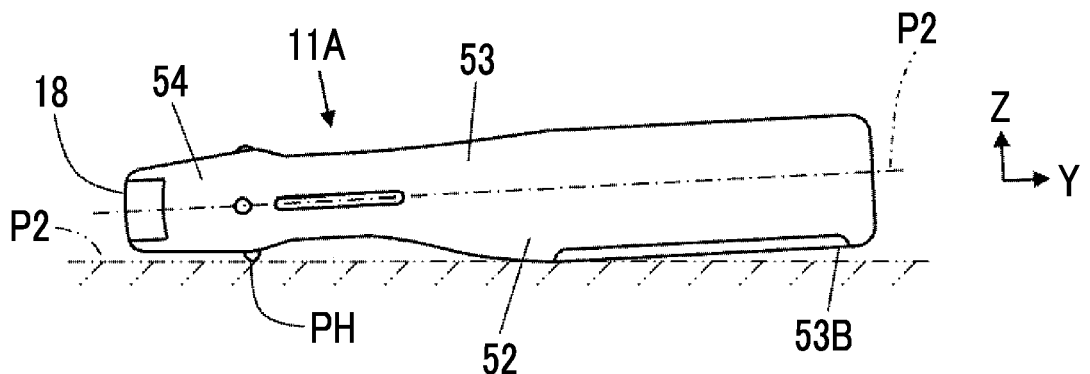
FIG. 9 is a side view of the ultrasound probe in a case where a protrusion is brought into contact with a placing surface in Embodiment 2 of the invention.

As shown in FIG. 8, in a case where the ultrasound probe 11A is placed on the placing surface P1 with the probe support surface 53B being brought into contact with the flat placing surface P1, a surface of the housing 52 in a portion positioned on the transducer array accommodation portion 54 side with respect to the probe support surface 53B is separated from the placing surface P1, and a surface of the protrusion of the housing 52 is separated from the placing surface P1. As shown in FIG. 9, in a case where ultrasound probe 11A is placed on the placing surface P1 with the protrusion PH being brought into contact with the placing surface P1, the ultrasound probe 11A is in such a posture that the surface of the transducer array accommodation portion 54 is separated from the placing surface.

For this reason, with the ultrasound probe 11A according to Embodiment 2 of the invention, in a case where the ultrasound probe 11A is placed on the placing surface P1 in such a manner that the probe support surface 53B is directed toward the placing surface P1 side, even though the transducer array accommodation portion 54 is inclined to the −Z direction side, the surface of the transducer array accommodation portion 54 is separated from the placing surface P1. Thus, in a case where the ultrasound gel is applied to the acoustic lens 18 and the transducer array accommodation portion 54, and the ultrasound probe 11A is placed on the placing surface P1, it is possible to more reliably restrain the placing surface P1 from being soiled due to the ultrasound gel being stuck to the placing surface P1. It is also possible to restrain the ultrasound gel itself from being soiled due to the ultrasound gel applied to the ultrasound probe 11A being stuck to the placing surface P1.

Embodiment 3

In the ultrasound probe 11 of Embodiment 1 and the ultrasound probe 11A of Embodiment 2, although each of the probe support surface 13B of the grip portion 13 of the housing 12 and the probe support surface 53B of the grip portion 53 of the housing 52 is parallel to the probe reference surface P2 defined in each of the ultrasound probe 11 and the ultrasound probe 11A, the invention is not limited thereto.

Figure 10:
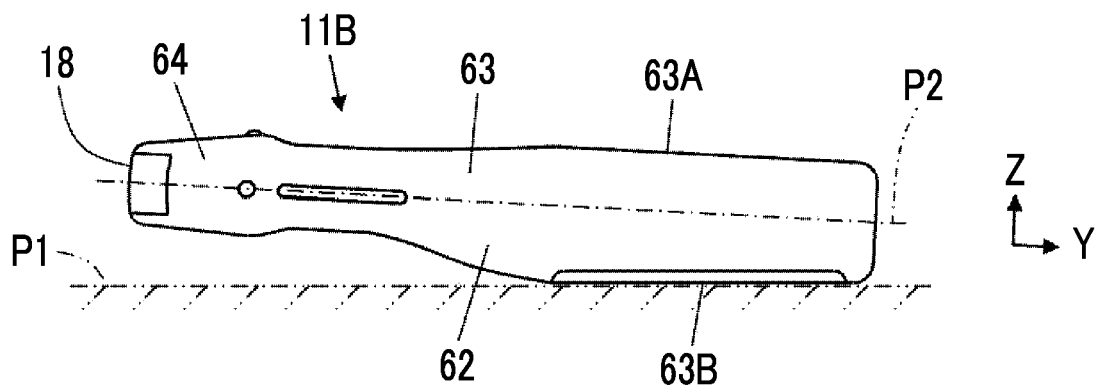
FIG. 10 is a side view of an ultrasound diagnostic apparatus according to Embodiment 3 of the invention.

FIG. 10 shows an ultrasound probe 11B according to Embodiment 3 of the invention. The ultrasound probe 11B comprises a housing 62 instead of the housing 12 in the ultrasound probe 11 of Embodiment 1 shown in FIGS. 1 to 4. As shown in FIG. 10, the housing 62 has a grip portion 63 that extends along a determined direction, and a transducer array accommodation portion 64 that is connected to an end portion of the grip portion 63 in the −Y direction. In the grip portion 63, a flat probe support surface 63B that is inclined with respect to the probe reference surface P2 passing through the center of the arrangement of a plurality of transducers in the transducer array 19 and extends in the arrangement direction of a plurality of transducers and the extension direction of the grip portion 63 is defined in a surface on the −Z direction side. The probe support surface 63B is inclined with respect to the probe reference surface P2 to be closer to the probe reference surface P2 as proceeding in the +Y direction and to be farther from the probe reference surface P2 as proceeding in the −Y direction.

For this reason, as shown in FIG. 10, in a case where the ultrasound probe 11B is placed on the placing surface P1 to bring the probe support surface 63B into contact with the placing surface P1, the probe reference surface P2 is brought into a state of being inclined with respect to the placing surface P1 such that the end portion of the transducer array accommodation portion 64 in the −Y direction is directed toward the +Z direction side. Thus, the transducer array accommodation portion 64 is easily separated from the placing surface P1.

With this, with the ultrasound probe 11B according to Embodiment 3, in a case where ultrasound gel is applied to the acoustic lens 18 and the end portion of the transducer array accommodation portion 64 in the −Y direction, and the ultrasound probe 11A is placed on the placing surface P1, it is possible to more reliably restrain the placing surface P1 from being soiled due to the ultrasound gel being stuck to the placing surface P1. It is also possible to restrain the ultrasound gel itself from being soiled due to the ultrasound gel applied to the ultrasound probe 11B being stuck to the placing surface P1.

EXPLANATION OF REFERENCES

1: ultrasound diagnostic apparatus
11, 11A, 11B: ultrasound probe
12, 52, 62: housing
13, 53, 63: grip portion
13A, 53A, 63A: probe operating surface
13B, 53B, 63B: probe support surface
14, 54, 64: transducer array accommodation portion
15B: operation switch
16A, 16B, 16C: indicator
17, 57: battery cover
17A: flat surface
18: acoustic lens
19: transducer array
20: circuit substrate
21: battery
31: transmission unit
32: reception unit
33: ultrasound transmission and reception controller
34, 42: wireless communication unit
47: communication controller
36: probe controller
37: ultrasound probe-side processor
38: amplification unit
39: AD conversion unit
40: beamformer
41: diagnostic apparatus body
43: signal processing unit,
44: image processing unit
45: display controller
46: display unit
48: body controller
49: operating unit
50: storage unit
51: diagnostic apparatus body-side processor
G: center of gravity
P1: placing surface
P2: probe reference surface
PH: protrusion

What is claimed is:

1. An ultrasound probe comprising:
a transducer array in which a plurality of transducers are arranged; and
a housing in which the transducer array is accommodated,
wherein the housing has
a grip portion that extends in an extension direction,
a transducer array accommodation portion that is connected to one end portion of the grip portion in the extension direction and accommodates the transducer array, a probe support surface that is defined in a surface on the other end portion side of the grip portion in the extension direction, extends along the extension direction and has a flat shape, and
a probe operating surface that is defined in a surface of another end portion of the grip portion and is directed in a direction opposite to the probe support surface,
wherein a probe reference surface that passes through a center of the arrangement of the plurality of transducers in the transducer array and extends in an arrangement direction of the plurality of transducers and the extension direction of the grip portion is positioned between the probe support surface and the probe operating surface,
a distance between the probe reference surface and the probe support surface is greater than a distance between the probe reference surface and the probe operating surface,
a center of gravity of the ultrasound probe is positioned on the other end portion side of the grip portion in the extension direction of the grip portion, and is positioned between the probe support surface and the probe reference surface,
in a case where the ultrasound probe is placed on a flat placing surface with the probe support surface being brought into contact with the flat placing surface, the ultrasound probe is in such a posture that a surface of the housing in a portion positioned on the transducer array accommodation portion side with respect to the probe support surface is separated from the flat placing surface, and the distance between the probe reference surface and the probe support surface being greater than the distance between the probe reference surface and the probe operating surface forms an asymmetric shape of the grip portion about the probe reference surface and results in an advantage of separating the transducer array accommodation portion from the flat placing surface when the ultrasound probe is placed on the flat placing surface while also improving a user's grip on the grip portion.

2. The ultrasound probe according to claim 1, further comprising:

a battery that is incorporated in the other end portion of the grip portion.

3. The ultrasound probe according to claim 2, further comprising:

an operation switch and an indicator disposed in the probe operating surface.

4. The ultrasound probe according to claim 2, wherein the housing has a protrusion that is formed at a position on a surface on the same side as the probe support surface about the probe reference surface and close to the transducer array accommodation portion with respect to the probe support surface, and the ultrasound probe is in such a posture that, in a case where the ultrasound probe is placed on the flat placing surface with the probe support surface being brought into contact with the flat placing surface, a surface of the protrusion is separated from the flat placing surface, and in a case where the ultrasound probe is placed on the flat placing surface with the protrusion being brought into contact with the flat placing surface, a surface of the transducer array accommodation portion is separated from the flat placing surface.

5. The ultrasound probe according to claim 1, further comprising:

an operation switch and an indicator disposed in the probe operating surface.

6. The ultrasound probe according to claim 1, wherein the housing has a protrusion that is formed at a position on a surface on the same side as the probe support surface about the probe reference surface and close to the transducer array accommodation portion with respect to the probe support surface, and the ultrasound probe is in such a posture that, in a case where the ultrasound probe is placed on the flat placing surface with the probe support surface being brought into contact with the flat placing surface, a surface of the protrusion is separated from the flat placing surface, and in a case where the ultrasound probe is placed on the flat placing surface with the protrusion being brought into contact with the flat placing surface, a surface of the transducer array accommodation portion is separated from the flat placing surface.

\* \* \* \* \*